(12) United States Patent
Alexandre

(10) Patent No.: US 9,008,794 B2
(45) Date of Patent: Apr. 14, 2015

(54) SENSOR DEVICE FOR TREATMENT AND REMOTE MONITORING OF VITAL BIOLOGICAL PARAMETERS

(75) Inventor: Alberto Alexandre, Catanzaro (IT)

(73) Assignees: Antonio Alexandre, Catanzaro (IT); Alvise Alexandre, Catanzaro (IT); Andrea Alexandre, Treviso (IT)

( * ) Notice: Subject to any disclaimer, the term of this patent is extended or adjusted under 35 U.S.C. 154(b) by 0 days.

(21) Appl. No.: 13/984,545

(22) PCT Filed: Feb. 14, 2012

(86) PCT No.: PCT/IB2012/050671
§ 371 (c)(1), (2), (4) Date: Oct. 7, 2013

(87) PCT Pub. No.: WO2012/110954
PCT Pub. Date: Aug. 23, 2012

(65) Prior Publication Data
US 2014/0024881 A1   Jan. 23, 2014

(30) Foreign Application Priority Data
Feb. 14, 2011 (IT) .............................. VI2011A0027

(51) Int. Cl.
*A61N 1/18* (2006.01)
*A61N 2/00* (2006.01)
(Continued)

(52) U.S. Cl.
CPC .............. *A61N 2/002* (2013.01); *A61B 5/6804* (2013.01); *A61B 5/0022* (2013.01); *A61N 1/36* (2013.01); *A61N 5/0625* (2013.01); *A61B 5/02438* (2013.01); *A61B 5/0816* (2013.01); *A61B 5/11* (2013.01); *A61B 5/14552* (2013.01); *A61B 2562/164* (2013.01)

(58) Field of Classification Search
USPC .................................. 607/115, 148, 152, 156
See application file for complete search history.

(56) References Cited

U.S. PATENT DOCUMENTS 6,278,092 B1 * 8/2001 Wu ................................ 219/549
6,321,388 B1 * 11/2001 Hildebrandt ........................ 2/69
(Continued)

FOREIGN PATENT DOCUMENTS

| DE | 202011107065 | 12/2011 |
|----|--------------|---------|
| WO | 0240091      | 5/2002  |
| WO | 2009153730   | 12/2009 |

*Primary Examiner* — Christopher D Koharski
*Assistant Examiner* — Michael Carey
(74) *Attorney, Agent, or Firm* — Themis Law

(57) ABSTRACT

A portable multi-sensor device includes a substantially sheet-like and at least partially flexible unit support element, a garment to be worn by a user and to be removably associated with the support element, a plurality of sensors, adapted to detect biological and/or vital parameters on the body of a user and transduce them into electric signals, at least one of which is incorporated in the unit support element, a transceiver for remote transmission of the electric signals to a remote monitoring center, a processing and control unit for processing and controlling the electric signals, therapeutic treatment elements associated with the unit support element and designed to contact one part of the wearer's body. The therapeutic treatment elements are electrically connected to the processing and control unit to be controlled thereby and to provide therapeutic and/or thermal therapeutic treatment to an area of the body.

13 Claims, 2 Drawing Sheets

(51) Int. Cl.
*A61B 5/00* (2006.01)
*A61N 1/36* (2006.01)
*A61N 5/06* (2006.01)
*A61B 5/024* (2006.01)
*A61B 5/08* (2006.01)
*A61B 5/11* (2006.01)
*A61B 5/1455* (2006.01)

(56) References Cited

U.S. PATENT DOCUMENTS

| | | | |
|---|---|---|---|
| 2003/0220679 A1* | 11/2003 | Han | 607/142 |
| 2010/0063556 A1* | 3/2010 | Oestreich | 607/3 |
| 2010/0094146 A1 | 4/2010 | Coulston | |
| 2010/0286545 A1* | 11/2010 | Wolfe et al. | 600/534 |

* cited by examiner

SENSOR DEVICE FOR TREATMENT AND REMOTE MONITORING OF VITAL BIOLOGICAL PARAMETERS

FIELD OF THE INVENTION

The present invention generally finds application in the field of electromedical equipment and particularly relates to a multi-sensor device for remote detection of biological and vital parameters, for remote diagnosis in patients, elderly or people undergoing remote analysis and examination.

A further aspect of the invention relates to a remote monitoring system in patients and users in general, which incorporates such device.

BACKGROUND ART

Devices have been long known for remote monitoring and diagnosis of bioelectric, biological, neuro-orthopedic and functional parameters, such as heartbeat rate, respiratory rate, body temperature, position and balance in elderly individuals with particular devices, or in users in general to be monitored for a given time.

These physiological and vital parameters and signs may be subject to remote monitoring, i.e. detection and storage by a control unit located next to the patient, and then transmitted via radio, telephone or the Internet to a diagnostics service center, such as Holter devices for ECG recording in active individuals.

The control unit typically has an emergency button which is used to send an alarm signal to a local receiving station (in most cases such receiving station being located in the user's house) and which transmits it to a service center.

This system has a satisfactory operation as long as the user can accomplish his/her tasks by his/herself, and is nearly useless if the patient feels faint or has an accident.

Vital sign detection devices are known, e.g. resembling large watches containing a number of sensors therein, such as a motion sensor (accelerometer) for detecting any fall, an optical cell located at an aperture where the user periodically places his/her finger, if he/she can do it, for heartbeat detection, a finger plethysmograph for measuring oxygen in blood, a pushbutton for emergency calls.

With this system, proper detection and monitoring of parameters entirely relies on the patient. Also in this case, if the user feels faint, the fall alarm might only be useful. Nevertheless, since the device is locally placed on the wrist, i.e. the part of the body that is most exposed to abrupt movements, rotations and bends, this alarm would also be ineffective.

Other prior art remote monitoring devices are disclosed, for instance, in U.S. Pat. No. 6,551,252, WO03/034890, U.S. Pat. No. 4,827,943, U.S. Pat. No. 6,656,125, U.S. Pat. No. 6,047,203, U.S. Pat. No. 7,173,437, WO2010/038176, US2011/087080, WO2009/036329, US2005/096513. The devices disclosed in these prior art documents are designed to be worn for a rather long time and essentially consist of a corset or a chest belt, which is much more comfortable and reliable.

Another commercially available type of such devices consists of garments, such as t-shirts, belts or corsets having sensors integrated in a fabric and associated with an electronic remote control circuit, as disclosed, for instance, in WO2005032447.

Measurements performed with these prior art devices have proven poor reliability. This is because electrodes and sensors typically comprise a conductive yarn, e.g. woven silver threads. Nevertheless, once the garment has been washed a few times, metal fibers separate from the base fabric and uncomfortably contact the skin. Furthermore, especially elderly or ill users are reluctant to wear the garment, which shall be rather close-fitting for easy acquisition of biological data.

One general drawback of prior art detection devices is that they cannot provide a real-time therapeutic action to the patient, at the area of the body upon which they are worn.

A further drawback of these detection devices is their poor portability by users and the difficulty to adapt them to garments. The user is often an active and dynamic person, who works and may travel miles to reach his/her working place, and would find it uncomfortable and inconvenient to use a rigid and complex apparatus.

Furthermore, these devices cannot be easily modified or adapted to particular conditions of use, e.g. with a light garment, or a garment used for leisure time.

DISCLOSURE OF THE INVENTION

A main object of the present invention is to obviate the above drawbacks, by providing a remote vital and biological parameter monitoring device that is highly efficient and relatively cost-effective.

A particular object is to provide a Multi-sensor therapeutic device that affords monitoring of vital signs of a patient and real-time intervention on the patient with a therapeutic action, modulated according to the detected parameters.

A further object is to provide a device for monitoring biometric and vital parameters, that can be more easily and comfortably worn as compared with prior art bustiers, belts, corsets, with improved wearability by users, possibly elderly people, who have just undergone surgery or have problems in moving.

Yet another object is to provide a device for monitoring biometric and vital parameters that can be adapted to various types and forms of garments, for more flexible use by active individuals.

These and other objects, as better explained hereafter, are fulfilled by a device as defined in claim 1.

Advantageous embodiments of the invention are described in the dependent claims.

BRIEF DESCRIPTION OF THE DRAWINGS

Further features and advantages of the invention will be more readily apparent upon reading of the detailed description of a preferred non-exclusive embodiment of a Multi-sensor device for remote electronic monitoring of biological and vital parameters, which is shown as a non-limiting example with the help of the annexed figures, in which.

DETAILED DESCRIPTION OF ONE PREFERRED EMBODIMENT

Referring to the accompanying figures, the device of the invention, generally designated by numeral 1, may be used for remotely monitoring a general user and for providing a physical therapy to the area of the body of the user where the device is applied from time to time.

Figure 1:
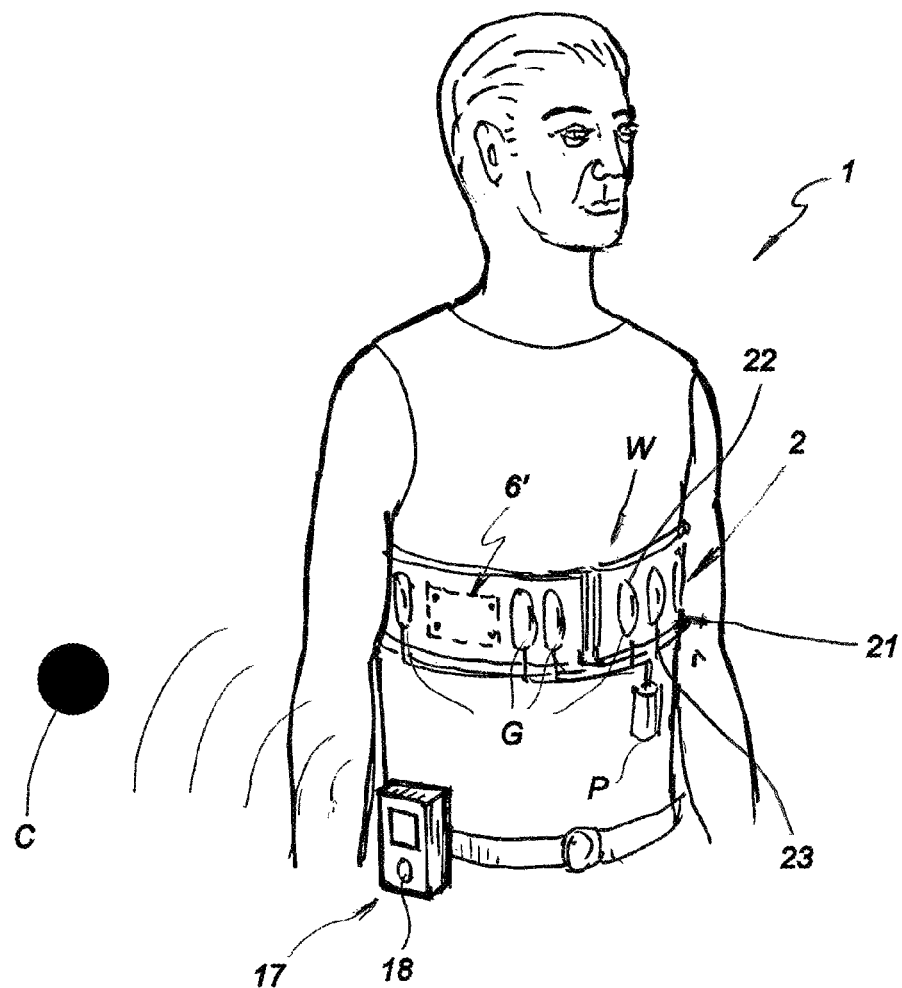
FIG. 1 is a general perspective view that diagrammatically shows a device of the invention associated with a garment worn by a user.
Figure 2:
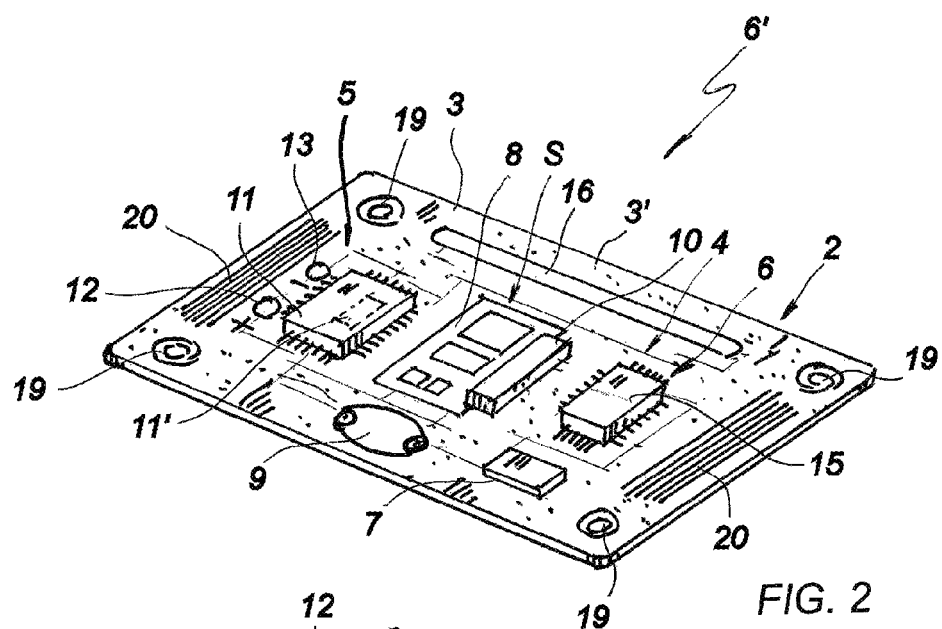
FIG. 2 is a top perspective view of a device of the invention.
Figure 3:
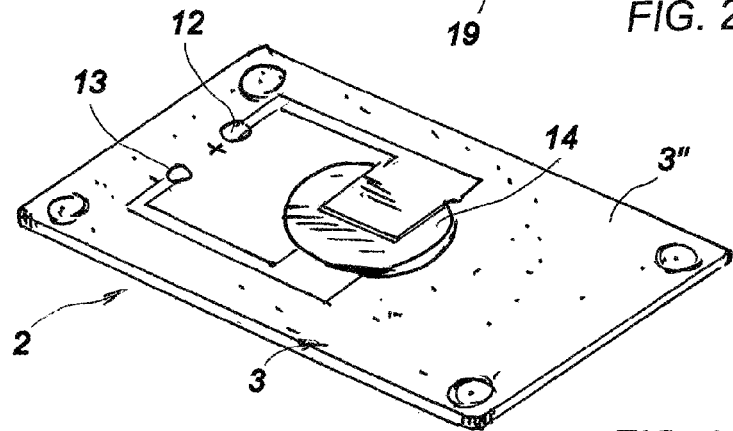
FIG. 3 is a bottom perspective view of the device of FIG. 2.

As shown in FIG. 1, the device essentially comprises a support element 2 with a plurality of sensors, generally referenced S, attached thereto, for detecting biological and/or vital parameters on the body of a user and for transducing them into electric signals, as described in greater detail hereinafter.

The device further comprises processing and control means 6' for detecting and processing the electric signals generated by the sensors S.

The processing and control means 6' are associated with the unit support element 2 in a stationary or removable fashion, e.g. are incorporated therein.

Preferably, the device 1 comprises a garment W adapted to be worn by a user, such as a bustier, a corset, a t-shirt or any other garment having means for removable attachment thereto of the unit element 2, with the processing and control means 6' entirely integrated therein.

Preferably, the processing and control means 6' comprise a relatively thin sheet-like card 3, which is at least partially flexible and/or deformable, and adapted to conform to the outer surface of the user's body.

Conveniently, the card 3 has a front surface 3' and a rear surface 3" which are substantially parallel, and have the plan shape and size of a credit card, e.g. 40×30×3 mm.

The sensors S are attached to the front surface 3' to be oriented towards the user's body and generate respective analog and/or digital electric signals, as described in greater detail below. Preferably, the above mentioned surface 3', which is designed to contact the user's skin, is covered by a layer of soft and biocompatible material to avoid irritation.

Advantageously, the device 1 also comprises means 21 for therapeutic treatment of the area of the human body in contact with the device 1, which are associated with the support element 2 and are designed to contact a part of the user's body.

The therapeutic treatment means 21 are electrically connected to the processing and control means 6' to be controlled thereby and to provide, for instance, an orthopedic and/or thermal therapeutic treatment to the area of the body with which they are in contact.

The processing and control means 6' may include a printed circuit board 4 placed on the front surface 3' of the card 3, and connected with the sensors S and other electronic components, essentially consisting of electronic circuits 5 for processing and control of the electric signals generated by the sensors S and for conversion thereof into digital electric signals, as well as means for remote transmission of the digital signals to a remote monitoring center, schematically designated as C.

Furthermore, the therapeutic treatment means 21 may include at least one first electrode 22, preferably two first electrodes 22, which are adapted to contact the part of the human body to provide a predetermined voltage and cause a transcutaneous electrostimulation of such region of the body.

Particularly, the first electrodes 22 may be designed to generate a plurality of electrical pulses at skin level, which are designed to interact with the muscular tissue for electrostimulation thereof.

The frequency and duration of application of such pulses may be adjusted by the processing and control means 6' according to the type of treatment to be administered to the user.

Conveniently, the therapeutic treatment means 21 may include at least one second electrode 23, which is adapted to contact an additional area of the human body and release heat thereto for thermotherapy.

Particularly, the second electrode 23 may operate with an electrical resistor, infrared rays, Peltier effect, magnetic and/or electromagnetic fields or the like.

Furthermore, the processing and control means 6' may supply power to the second electrode 22 in a continuous or discontinuous manner, according to the treatment to be administered to the user.

In a particularly advantageous aspect of the invention, the processing and control means 6' may simultaneously supply power to the first electrodes 22 and the second electrode 23 for providing thermal therapy and electrostimulation at the same time.

Suitably, the first electrodes 22 and the second electrode 23 may be formed from the same base material.

Such base material may exhibit good electrical and thermal conductivity, to allow conduction of the electric signals transmitted by the processing and control means 6' and release of large amounts of heat.

Particularly, the base material may be selected from the group of conductive fabrics, namely composite conductive fabrics such as carbon fiber fabrics.

Advantageously, the garment W may have respective seats for stable and possibly removable accommodation of the electrodes 21, 22.

The garment W to be worn by a user is selected from the group comprising a belt, a bustier, a corset, an undershirt, a t-shirt, a glove, trousers, and has interface means for removable attachment thereof to the unit element 2.

Preferably, a garment W in the form of a bustier or corset may include orthopedic treatment means, such as air chambers G adapted to be inflated by an electric compressor P, for compression or distraction of the rib cage or the pelvis.

Conveniently, the compressor P is of such a size as to allow integration thereof in the garment W.

A non-limiting description of the sensors S is provided below, although sensors may be of many types, according to the type of user/patient to be monitored.

For example, the sensors S may comprise:
a heartbeat and rate detector,
a respiratory rhythm and rate detector,
a blood oxygen saturation detector,
a body temperature detector,
a step counter,
a position and motion sensor,
a fall sensor.

The above mentioned sensors may be integrated in the belt-like unit element 2 and/or wearable garment W in such a manner that the device 1 may operate at least partially even when the user wears only one of the element 2 and the garment W.

The heart rate and rhythm detector 7 may consist of a pair of flexible silver woven conductive electrodes or a layer of conductive silicone rubber, not shown.

The blood oxygen content sensor may consist of a reflective optical device 8, which processes the light reflected by the skin and the light reflected by the underlying tissues, to determine the amount of oxygen therein.

Possibly, the signal emitted by the optical device 8 may be processed to determine the interval between two reflected fluxes and hence the heartbeat rate. As a result, the blood oxygen saturation sensor and the heart rate sensor can be combined in a single optical device 8.

The breath detector, not shown, may use a piezoelectric or resistive elastomer as a sensitive element, which is adapted to generate an electric signal or a resistance variation in response to a deformation caused by a user's breath.

The temperature sensor 9 may consist of a sensor-chip comprising a thermistor sensitive to body temperature, which may be placed in direct contact with the user's skin.

The motion sensor 10 may consist of an acceleration sensor (MEMS) capable of detecting accelerations along the three Cartesian axes and may be also used as a fall sensor.

The analog electric signals generated by the sensors S are transmitted to the processing and control means 6', which essentially comprise a programmable microprocessor (EPROM) 11, to be converted into stable digital signals. The microprocessor 11 is programmed to set periodic sampling of all biometric and vital parameters to be monitored and to calculate mathematical and statistic data, such as the mean, the mean-square deviation, the variance of detected values.

Finally, an area of the microprocessor is dedicated to a mass storage (RAM) 11' for data storage and retrieval by the control system.

Terminals 12, 13 are provided at the ends of the electronic circuit 4, and are in turn connected to the terminals of a rechargeable battery 14, preferably placed on the rear surface 3" of the card 3.

The remote transmission means 6 for remote transmission of digital signals may include a transceiver or transponder 15 connected to a transceiving antenna 16.

Furthermore, the transceiver means 6 may be designed to transmit and receive the electric signals to and from display and interface means 24.

The display and interface means 24 may be a portable electronic apparatus, such as a remote control, a computer, a smartphone, a tablet or the like.

Particularly, the display and interface means 24 may be of wireless type to receive the electric signals transmitted by the transceiver means 6.

The display and interface means may be designed to display the received electric signals on a display or the like and allow the user to introduce biological data.

Such biological data may be transmitted to the transceiver means 6 which may in turn send it to the processing and control means 6' as soon as they receive it.

The biological data may be processed by the microprocessor 11 and later saved in the mass storage 11'.

Furthermore, such processing of the biological data by the processor 11, may change the power signals supplied to the therapeutic treatment means to change the action of the first electrode and/or second electrode.

The transponder 15 may be integrated in the card 3 or contained in an intermediate unit, located in an external container 17, like in FIG. 1, which resembles a portable telephone, and may be carried by the user and possibly held in a pocket or attached to a belt, and may transfer data via phone over a GPRS line. An emergency button 18 may be possibly provided on the container 17, to be actuated by the user when needed.

As an alternative, the card 3 with the processing and control means 6 may be integrated in the garment W or comprise removable anchor means for removably joining it to the garment W.

Such anchor means may consist of snap fasteners 19 arranged along the corners of the card 3, or Velcro® straps 20 fixed along the end edges of the card 3.

Of course, these anchor means may be replaced by other means, such as adhesives or magnetic plates, not shown.

With these anchor means, the card 3 and hence the device 1 as a whole, may be removably joined to any garment W or a bustier, a belt F or a corset.

The operation of the device 1 is as follows.

In a continuous fashion, or at predetermined time intervals, the microprocessor controls the sequential and periodic sampling of all parameters, i.e. heartbeat, body temperature, motion, oxygen saturation, step count, and any fall. These parameters are temporarily stored in the RAM storage 11' of the microprocessor 11. Statistic data is calculated at regular intervals, and periodically loaded and retrieved to and from the internal storage 11'.

A USB port may be possibly provided in the circuit 4, for connecting the microprocessor to a portable storage medium such as a pen drive, which may store the data to be directly transferred to a PC.

Should an alarm condition occur, the signal processed by the microprocessor 11 or possibly generated by pushing the emergency button on the container 17, will be immediately transmitted, in addition to the space coordinates of the transmitter worn by the user, by the transponder 15 over a GPRS line to the remote service center C, which will allow actions to be taken according to predetermined protocols.

Furthermore, a remote control or a similar device may be used to act upon the electric control circuits of the electrodes 21, 22, to provide an electrostimulation therapy and/or a thermal therapy, possibly with regular intervals being set to provide such therapies.

The service center C may request all stored data at any time, or download it from each user at a predetermined time, e.g. midnight.

In a second aspect, the invention relates to a system for remote monitoring of patients and users which comprises a garment adapted to be worn by a user, and to be removably joined to the above described portable Multi-sensor device, which may be in turn associated with an external GPRS/GPS module 17 for remote connection to a remote monitoring center C.

The device and the system of the invention are susceptible of many changes and variants within the inventive principle disclosed in the annexed claims.

All the details thereof may be replaced by other technically equivalent parts, and the materials may vary depending on different needs, without departure from the scope of the invention.

While the device and system have been described with particular reference to the annexed figures, the numerals referred to in the disclosure and claims are only used for the sake of a better intelligibility of the invention and shall not be intended to limit the claimed scope in any manner.

The invention claimed is:

1. A portable multi-sensor device (1) for treatment and remote monitoring of vital biological parameters comprising:
   a garment (W) designed to be worn by a user;
   a substantially sheet-like and at least partially flexible unit support element (2), adapted to be removably joined to said garment (W);
   a plurality of sensors (S), adapted to detect one or more of biological of vital parameters on a body of a user and transduce said one or more of biological of vital parameters into electric signals, at least one of said sensors (S) being incorporated in said unit support element (2);
   a transceiver (6) for remote transmission of said electric signals to a remote monitoring center (C);
   a processing and control unit (6') for processing and controlling said electric signals associated with said unit support element (2); and
   therapeutic treatment elements (21) associated with said unit support element (2) and designed to come into contact with a part of the user's body, said therapeutic treatment elements (21) being electrically connected to said processing and control unit (6') to be controlled thereby, wherein said therapeutic treatment elements (21) include at least one first electrostimulating electrode (22) adapted to contact respective areas of the user's body to provide a predetermined voltage for transcutaneous electrostimulation of such areas of the body and adapted to generate a plurality of electrical pulses at skin level, for electrostimulation of muscular tissues in a body region to be treated, wherein said therapeutic treatment elements comprise thermal treatment elements (21) and orthopedic treatment elements, said thermal treatment elements including at least one second electrode (23) of an electrical resistor, infrared rays, Peltier effect, or magnetic or electromagnetic fields adapted to contact an additional area of the user's body to release heat thereto, said orthopedic treatment elements comprising inflatable air chambers (G) for compression or distraction of a rib cage or pelvis, and a compressor integrated in said garment (W), wherein said processing and control unit (6') is integrated in said garment (W) and comprises a card (3) made of a relatively flexible synthetic material, which is adapted to conform to an outer surface of the user's body and has a substantially polygonal plan shape, wherein said garment has plurality of seats for stably accommodating said first and second electrodes, and wherein said unit support element (2) is a belt configured to be removably attached to said garment.

2. The portable multi-sensor device as claimed in claim 1, wherein said at least one first electrode (22) and said at least one second electrode (23) are made of a base material selected from the group consisting of conductive composite fabrics with carbon fiber.

3. The portable multi-sensor device as claimed in claim 1, wherein said garment is selected from the group consisting of a belt, a bustier, a corset, an undershirt, a t-shirt, a sweater, a glove, or trousers.

4. The portable multi-sensor device as claimed in claim 3, wherein said card (3) comprises removable anchor members (19, 20) for removable anchoring of said card to the belt, wherein said anchor members are selected from the group consisting of buttons, hook and loop, contact, or magnetic adhesives.

5. The portable multi-sensor device as claimed in claim 1, wherein several of said sensors (S) are anchored to said card (3) on a front surface (3') thereof, to face the user's body, the others of said sensors (S) being anchored to said unit support element (2).

6. The portable multi-sensor device as claimed in claim 1, wherein said sensors (S) comprise at least one sensor selected among the group consisting of a heart rate and rhythm detector (7), a respiratory rate and rhythm detector, a blood oxygen content detector (8), a temperature sensor (9), or a position and motion detector (10).

7. The portable multi-sensor device as claimed in claim 1, wherein said transceiver (6) includes at least one wireless transceiver or transponder (15) and a transceiving antenna (16).

8. The portable multi-sensor device as claimed in claim 1, wherein said transceiver (6) is adapted to transmit and receive said electric signals to and from a display and interface (24).

9. The portable multi-sensor device as claimed in claim 8, wherein said display and interface (24) is of a wireless type, to receive said electric signals from said transceiver (6), said display and interface (24) being adapted to display said electric signals on a display, and allow a user to enter biological data and transmit said biological data to said transceiver (6).

10. The portable multi-sensor device as claimed in claim 9, wherein said processing and controls unit (6') includes at least one programmable microprocessor (11) connected to one or more of said sensors (S) or said therapeutic treatment elements (21) and containing at least one mass storage unit (11') for storing said electric signals and said biological data transmitted by said display and interface (24), said at least one microprocessor (11) being connected to a rechargeable battery (14).

11. The portable multi-sensor device as claimed in claim 10, wherein said transceiver (6) is integrated in said card (3) or is installed in an intermediate portable unit (17) adapted to be worn by the user and electrically connected with said processing and control unit (6') and said therapeutic treatment elements (21).

12. The portable multi-sensor device as claimed in claim 11, wherein said intermediate unit (17) has a GPRS/GPS transmission and localization system and an emergency button (18).

13. The portable multi-sensor device as claimed in claim 5, wherein said front surface of said card is covered by a protective layer of a soft and biocompatible material, to avoid skin irritation of the user's epidermis.

* * * * *